United States Patent [19]

Shoesmith

[11] Plant 5,029

[45] Apr. 5, 1983

[54] CHRYSANTHEMUM NAMED BRUIN

[75] Inventor: May Shoesmith, Woking, England

[73] Assignee: Pan American Plant Company, Parrish, Fla.

[21] Appl. No.: 312,943

[22] Filed: Oct. 19, 1981

[51] Int. Cl.[3] ..... A01H 5/00

[52] U.S. Cl. ..... Plt./78

[58] Field of Search ..... Plt./78, 75

*Primary Examiner*—Robert E. Bagwill

*Attorney, Agent, or Firm*—Chas. W. Rummler

[57] ABSTRACT

A new chrysanthemum cultivar suitable for year around four inch pot production and for Fall garden culture, distinguished by its profuse production of bright yellow button-type flowers of a relatively small size and an on-plant lasting quality of three to four weeks.

4 Drawing Figures

BACKGROUND OF THE NEW PLANT

This plant was discovered in 1976 as a seedling of unknown parentage growing among a group of miscellaneous seedlings which were originated by me and maintained at West Chicago for observation, test and breeding purposes. The profuse production by this plant of very attractive, small, pom pom shaped, button-type bright yellow flowers, caused it to be selected for testing. Extensive asexual propagation, by cuttings and under my direction, through successive generations, has shown that this new plant will be an excellent garden chrysanthemum, as well as having an ability for year around production in small four to four and a half inch pots, generally with an eight-week response. Culture of this new plant through successive generations has also shown that its novel characteristics hold true and are firmly fixed. Commercial scale production of this plant is now being done at Parrish and Cortez, Fla.

DESCRIPTION OF THE DRAWINGS

This new cultivar of chrysanthemum is illustrated by the accompanying drawings, of which sheet 1 is a full color photographic view showing a field of the plants in full bloom; sheet 2 is a photographic close-up view of flowers of this new plant which has been hand painted to show the true colors of the blooms; sheet 3 is a machine copy showing the top side of typical leaves of this new variety; and sheet 4 is a machine copy of the same leaves but showing the bottom side thereof.

DESCRIPTION OF THE NEW PLANT

The following is a detailed description of my new chrysanthemum cultivar based upon observations made in the Spring of 1981 of plants grown at West Chicago, Ill., the color designations being according to The R.H.S. Colour Chart published by The Royal Horticultural Society of London, England.

THE PLANT

Origin: Seedling.
Parentage: Unknown.
Classification:
- *Botanic.*—*Chrysanthemum morifolium.*
- *Commercial.*—Garden Mum.

Form: Perennial herbaceous bush of mound shape.
Height: 1 to 1.5 meters.

Growth: Vigorous and strong with rapid growth rate.
Branching character: Normal for chrysanthemums.
Foliage:
- *Quantity.*—Abundant.
- *Size of leaf.*—From small to about 70 mm. long and about 50 mm. wide.
- *Shape.*—Ovate with cleft margins.
- *Texture.*—Leathery.
- *Venation.*—Pinnate.
- *Color.*—Upper side — 147A. Under side — 147B.
- *Petioles.*—Length — About 20 mm.
- *Rachis.*—About 70 mm. long.
- *Leaflets.*—Few in number and of various sizes.

THE BUD

Form: Globular.
Size: The size varies in both diameter and length.
Opening rate: Typical chrysanthemum.
Color of florets:
- *When phyllaries first divide.*—9A.
- *When petals begin to unfurl.*—9A.

Phyllaries:
- *Number.*—About 13.
- *Shape.*—Lanceolate.

Peduncle: The length varies.
- *Aspect.*—Pubescent.
- *Character.*—Strong.
- *Color.*—147C.

THE FLOWER

Blooming habit: Intermittent and blooming profusely in the Fall.
Blooms:
- *Size.*—Small. Diameter — About 20 to 30 mm. Depth — About 15 mm.
- *Borne.*—Cyme.
- *Shape.*—When bloom first opens — Cup-shaped. When bloom matures — A small pom pom, button type inflorescence borne on a receptacle surrounded by an involucre of bracts.

Petalage:
- *Ray florets.*—Many in number.
- *Disc florets.*—Very few.
- *Arrangement.*—Imbricated.
- *Form.*—Oblanceolate with truncate and incised apex and entire margins.

Texture: Soft.
Appearance: Satiny.

Color:
*Top side.*—9A.
*Reverse side.*—9C.
Peduncle: Strong and of various lengths.
*Color.*—147C.
Effect of ambient conditions: Color of the bloom varies slightly with temperature and light intensity.
Persistence: The florets hang on and dry.
Fragrance: Typical chrysanthemum.
Lasting quality:
*On plant.*—Three to four weeks.

REPRODUCTIVE ORGANS

Stamens:
*Number.*—Five.
*Arrangement.*—Syngenesious.
*Anthers.*—Size — Insignificant. Color — Yellow.
*Filaments.*—Length — Insignificant. Color — Yellow.
*Pollen.*—Color — Yellow.
Pistils:
*Number.*—One for each floret.

*Styles.*—Length — Insignificant. Color — Yellow.
Stigmas:
*Color.*—Yellow.
Ovaries: Inferior bicarpellate.

This plant is a new and distinct bright yellow button-type chrysanthemum for year around production in small pots of four to four and a half inches diameter and the plant generally has an eight-week response. This plant also makes an excellent garden mum and if planted as vegetative cuttings and pinched until flower initiation, this plant will make an excellent yellow mound of color in the Fall.

I claim:

1. A new and distinctive chrysanthemum cultivar, substantially has herein shown and described, characterized by its small button-type inflorescence of pom pom shape and a distinct bright yellow color, by its capability for year around production in small pots, and its profuse production of blooms.

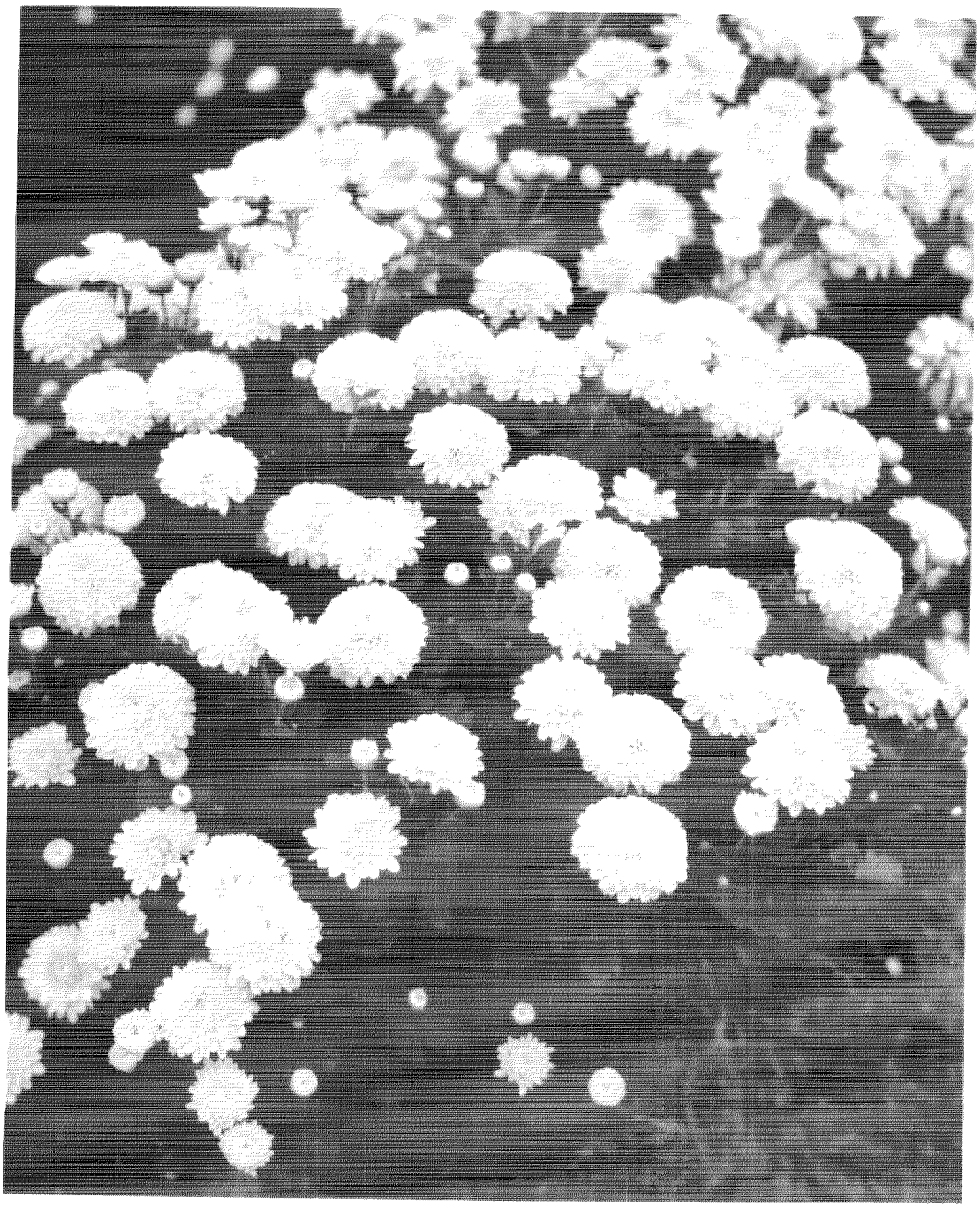

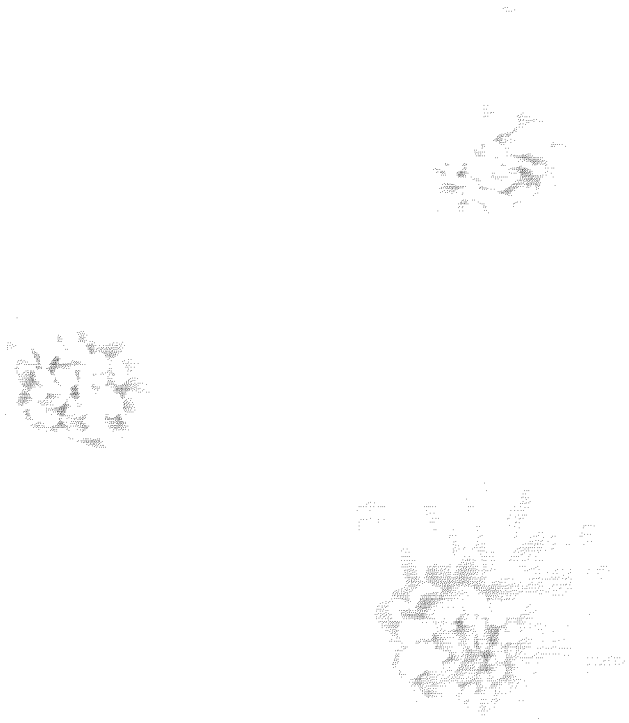

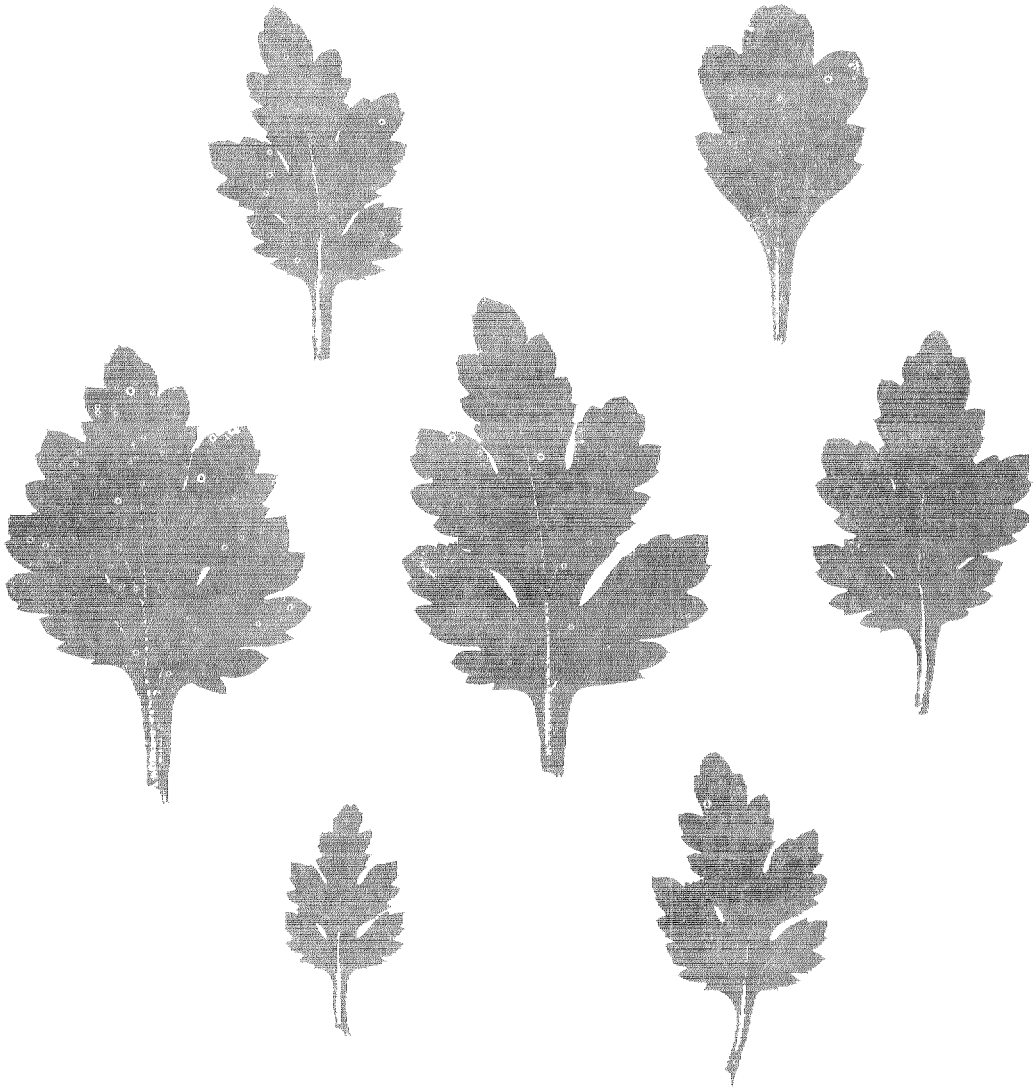

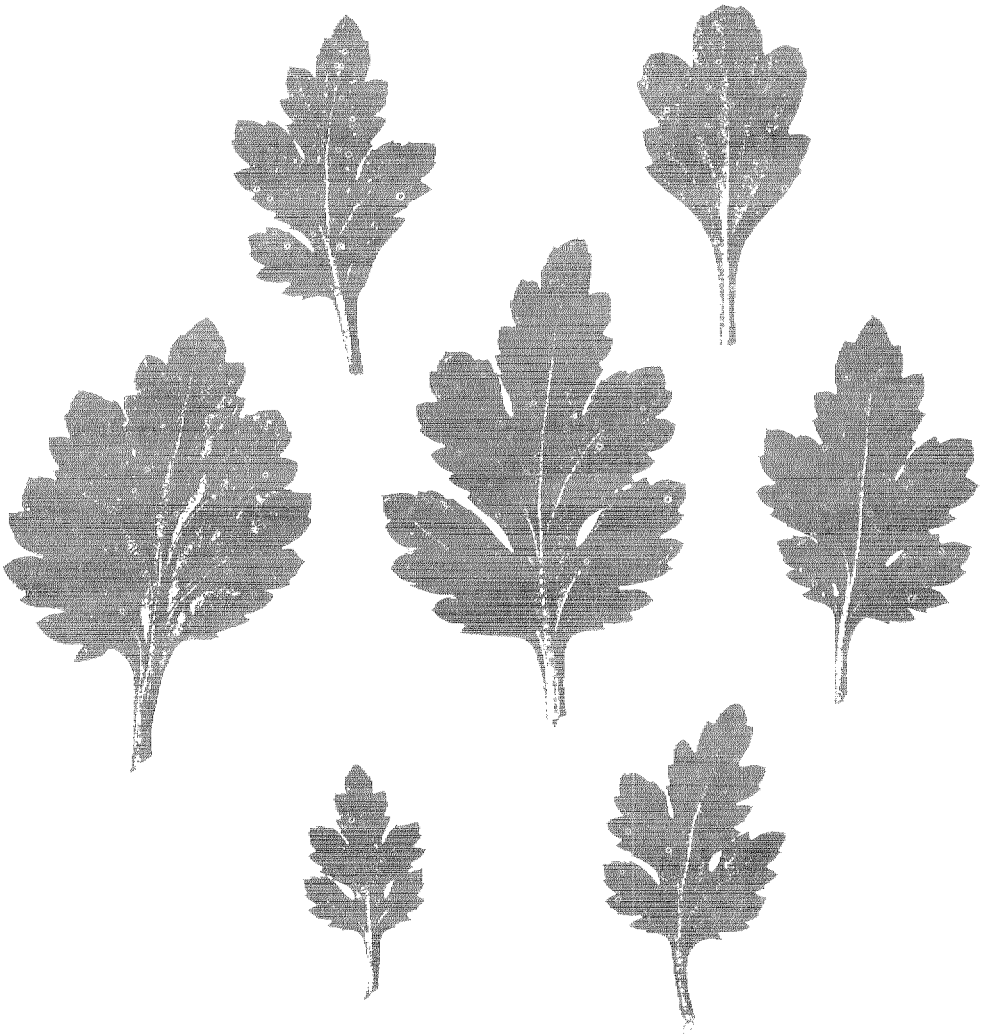

* * * * *